United States Patent [19]

Mueller et al.

[11] Patent Number: 4,992,588
[45] Date of Patent: Feb. 12, 1991

[54] PREPARATION OF O-ACYLAMINOMETHYLBENZYL HALIDES

[75] Inventors: Josef Mueller, Ludwigshafen; Walter-Weilant Wiersdorff, Mutterstadt; Werner Kirschenlohr, Ludwigshafen; Gerd Schwantje, Wachenheim, all of Fed. Rep. of Germany

[73] Assignee: BASF Aktiengesellschaft, Ludwigshafen, Fed. Rep. of Germany

[21] Appl. No.: 761,337

[22] Filed: Jul. 31, 1985

Related U.S. Application Data

[63] Continuation of Ser. No. 467,829, Feb. 18, 1983, abandoned.

[30] Foreign Application Priority Data

Feb. 25, 1982 [DE] Fed. Rep. of Germany ....... 3206660

[51] Int. Cl.$^5$ .................. C07C 233/66; C07C 233/13
[52] U.S. Cl. .................... 564/185; 564/189; 564/214; 564/219
[58] Field of Search ............ 564/189, 214, 219, 185

[56] References Cited

U.S. PATENT DOCUMENTS

| | | | |
|---|---|---|---|
| 2,100,822 | 11/1937 | Spurlin | 570/198 |
| 3,520,930 | 7/1970 | Clark et al. | 564/185 X |
| 3,937,730 | 2/1976 | Vogel et al. | 564/214 |
| 4,062,891 | 12/1977 | Remy | 564/219 |
| 4,311,858 | 1/1982 | Chupp | 564/214 |
| 4,322,553 | 3/1982 | Chupp | 564/211 X |
| 4,348,223 | 9/1982 | Grove | 564/214 X |

FOREIGN PATENT DOCUMENTS 2072654 10/1981 United Kingdom ............... 564/214

OTHER PUBLICATIONS

Braun et al., CA 20:391 (1926).
Haginiura et al., CA 54:11025e (1960).
Braun and Reich, Annalen, 445 (1925), 240.
Haginiwa et al., J. Pharm. Soc. Japan, 79 (12) (1959), 1578-1581.

*Primary Examiner*—Carolyn S. Elmore
*Attorney, Agent, or Firm*—Keil & Weinkauf

[57] ABSTRACT

O-acrylaminomethylbenzyl halides (I)

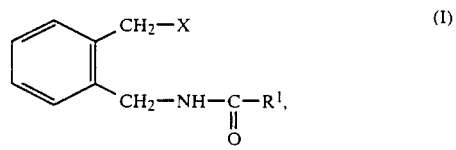

in which X is Cl or Br and $R^1$ is alkyl or aryl, are obtained by reacting an o-aminomethylbenzyl alkyl ether (II)

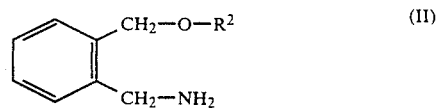

with an acylating agent, and then reacting the resulting acid amide, preferably without intermediate isolation, with an aqueous hydrohalic acid.

2 Claims, No Drawings

PREPARATION OF O-ACYLAMINOMETHYLBENZYL HALIDES

This application is a continuation of application Ser. No. 467,829, filed on Feb. 18, 1983, and now abandoned.

The present invention relates to a novel process for the preparation of o-acylaminomethylbenzyl halides of the general formula I

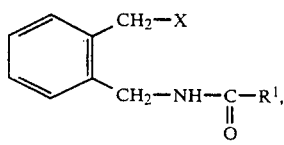

where X is halogen and $R_1$ is an aliphatic, cycloaliphatic, araliphatic or aromatic radical.

Compounds of the type I and their preparation have been described by Braun and Reich, Annalen, 445 (1925), 240, and by Haginiwa et al., J. Pharm. Soc. Japan, 79 (12) (1959), 1578 to 1581.

Thus, for example, o-aminomethylbenzyl ethyl ether can be reacted with concentrated, aqueous hydrohalic acid, to exchange the ether radical for chlorine or bromine, only under superatmospheric pressure and at a high temperature. However, this procedure has not given a pure product.

Only by carrying out the reaction with gaseous hydrogen chloride, in alcoholic solution, was it possible to isolate the desired chlorine compound as the hydrochloride. After liberating the chlorinated base, which is very sensitive, probably because of its tendency to undergo a cyclization reaction, the acyl radical in the form of a benzoyl radical was introduced:

U.S. Pat. No. 4,311,858 describes the cleavage of an N-(alkoxymethyl)-acylamine A with 37% strength hydrochloric acid at room temperature, the corresponding N-(chloromethyl)-acylamine B being isolated

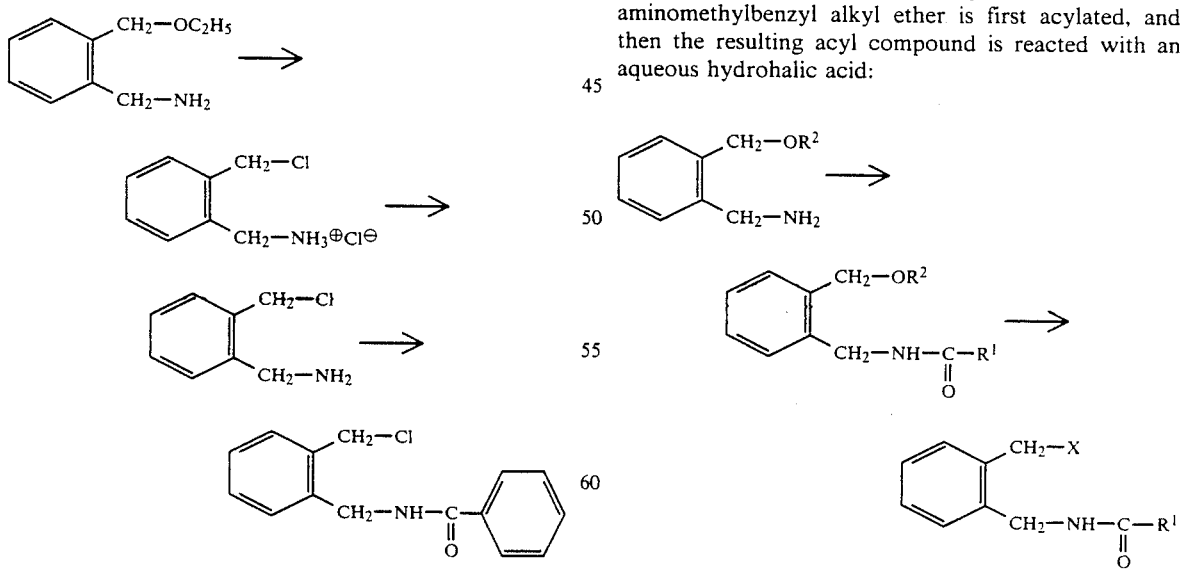

It is stated explicitly (page 2, lines 38 to 43 and 57 to 61) that A is an amidoaminal, which is known to be sensitive to hydrolysis, and that therefore the reaction is carried out at a low temperature. Thus, the teaching of the above U.S. Patent consists not in the recognition of the fact that the ether can be cleaved but in the fact that B is stable under the reaction conditions, which could not be foreseen.

It is an object of the present invention to carry out a cleavage reaction with a specific alkyl benzyl ether, without the amide structure which is also present undergoing cleavage. According to U.S. Pat. No. 2,100,822, the cleavage of benzyl ethers can be carried out successfully only at above 100° C., using concentrated hydrochloric acid. Under these conditions, however, amides readily undergo cleavage (Houben-Weyl 11/1, page 927). It was therefore surprising that cleavage of benzyl ethers could be carried out in accordance with the invention, using aqueous hydrochloric acid, without the amide group undergoing hydrolysis.

We have found that this object is achieved, and that the ether cleavage can be carried out with aqueous hydrohalic acid at a low temperature, if the o-aminomethylbenzyl alkyl ether is first acylated, and then the resulting acyl compound is reacted with an aqueous hydrohalic acid:

The present invention therefore relates to the preparation of a compound (I) by a process wherein an o-aminomethylbenzyl alkyl ether of the general formula (II)

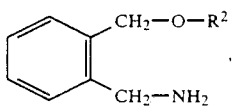

(II)

where $R^2$ is any aliphatic radical, in particular one of 1 to 4 carbon atoms, is converted to the corresponding acylaminomethylbenzyl ether of the general formula (III)

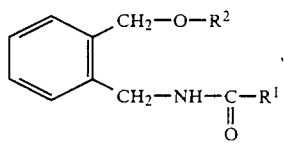

(III)

and this is then reacted with an aqueous hydrohalic acid to give the desired halogen compound (I).

Examples of radicals $R^1$ of economic interest are alkyl of 1 to 4 carbon atoms and phenyl, since these radicals are eliminated during further processing.

The compounds of the general formula (I) are important intermediates for the plant protection and pharmaceutical sectors. They can be used, for example, as intermediates for the preparation of o-aminomethylphenylacetic acid, which in turn is a building block of the semisynthetic antibiotic ceforanide:

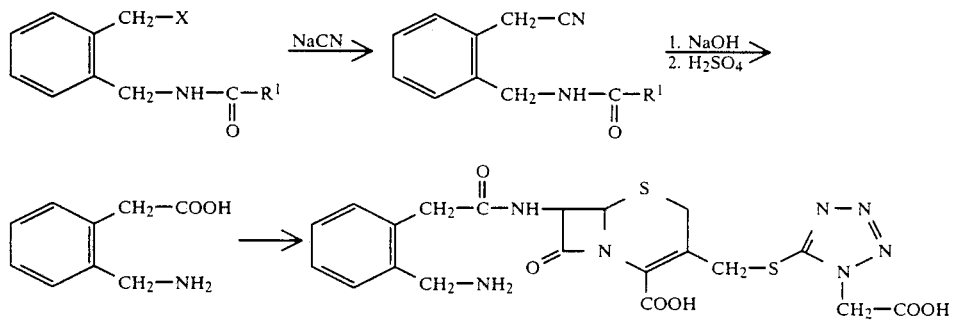

The o-aminomethylbenzyl alkyl ether (II) can be converted in a conventional manner, using a carboxylic acid chloride or anhydride in the presence or absence of a solvent. For practical reasons, $R^2$ is preferably methyl, but any other available compound containing a different ether radical may equally well be used.

Suitable solvents are toluene, xylene and chlorohydrocarbons, eg. methylene chloride. The reaction with the carboxylic acid halide is brought to completion with the aid of, for example, triethylamine or sodium carbonate, and can be carried out at from 0° to 200° C. The acylating agent may be added to the initially taken amine, or vice versa, at about 50° C., while cooling. Water is added and the aqueous phase is separated off, after which the acyl compound can be halogenated directly, or first crystallized after the solvent has been removed.

Conversion to the halogen compound is carried out using an aqueous hydrohalic acid, ie. HCl, HBr or if required HI. Reaction of the benzyl ether with aqueous hydrochloric acid has proved particularly simple. The HCl can be, for example, from 5 to 40% strength by weight, and the reaction is preferably carried out using excess, commercial hydrochloric acid (eg. 36% strength). The reaction can be effected batchwise or continuously, and is advantageously carried out in the presence of a further solvent, eg. methylene chloride, chloroform, dichloroethane or 1,2-dichloropropane, toluene or chlorobenzene, in which HCl should have a sufficiently high solubility. However, the reaction may also be carried out in the absence of a solvent.

The reaction takes place within a wide temperature range, but at above 100° C. relatively long residence times should be avoided. The reaction is preferably carried out at no higher than 80° C., in particular no higher than 60° C.

The two successive reactions are advantageously carried out in the same solvent, and the intermediate is not isolated (one-pot reaction). A substantial advantage of the invention over the conventional route is that it is possible to simplify the process in this manner.

Under the conditions according to the invention, the desired chlorine compounds I are obtained in very pure form; after the mixture has been neutralized and the aqueous phase separated off, the compounds readily crystallize out from the solvent used.

EXAMPLE 1 o-Acetamidomethylbenzyl methyl ether 604 g (4 moles) of o-aminomethylbenzyl methyl ether were dissolved in 1,500 ml of toluene, and 408 g (4 moles) of acetic anhydride were added to the stirred and cooled solution at a rate such that 60° C. was not exceeded. Stirring was continued, the mixture was neutralized with 424 g of 25% strength sodium hydroxide solution, and the aqueous phase was separated off. When the organic phase was evaporated down, 656 g (85% of theory) of the acylated benzyl ether of melting point 67°–68° C. crystallized.

o-Acetamidomethylbenzyl chloride

The 656 g (3.4 moles) of benzyl ether obtained were once again dissolved in 1,500 ml of toluene at 60° C., and the solution was stirred with 1,800 ml of concentrated hydrochloric acid for 5 hours. Thereafter, 1,350 ml of 25% strength sodium hydroxide solution were metered in at a rate such that 60° C. was not exceeded. The aqueous phase was separated off, 25% strength sodium hydroxide was added to the organic phase, the aqueous phase was again separated off and the chlorine compound was allowed to crystallize out. 550 g (82% of theory, based on benzyl ether) of product of melting point 69°–70° C. were obtained.

EXAMPLE 2

The procedure described in Example 1 was followed, except that the solution of the o-acetamidomethylbenzyl methyl ether in toluene was reacted directly with hydrochloric acid. In this case, 571 g (85% of theory) of product of melting point 68°–69° C. were obtained.

EXAMPLE 3 o-Acetamidomethylbenzyl methyl ether 604 g (4 moles) of o-aminomethylbenzyl methyl ether in 1,500 ml of toluene were initially taken, and 424 g (4 moles) of triethylamine were added. 314 g (4 moles) of acetyl chloride were then metered in at a rate such that 50° C. was not exceeded. After the addition was complete, stirring was continued for 1 hour at 60° C., after which 560 g of water were added to the stirred mixture, and the aqueous phase was then separated off. When the organic phase was evaporated down, 673 g (87.2% of theory) of the acetamide of melting point 68° C. crystallized out.

We claim:

1. A process for the preparation of an o-acylaminomethylbenzyl halide of the formula (I)

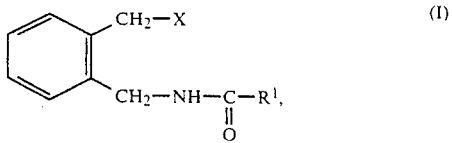

where X is a halogen and $R^1$ is an aliphatic or aromatic radical which comprises: first, reacting an o-aminomethylbenzyl alkyl ether of the formula (II)

where $R^2$ is alkyl with an acylating agent to give the corresponding acylaminomethylbenzyl alkyl ether and thereafter reacting said ether with an aqueous hydrohalic acid at a temperature no higher than 80° C. to give the corresponding halide (I), with both reactions being carried out in the same solvent and reaction vessel, and wherein said acylaminomethylbenzyl alkyl ether intermediate is not isolated prior to reaction with said hydrohalic acid.

2. A process according to claim 1, wherein said acylaminomethylbenzyl alkyl ether is reacted with said hydrohalic acid at a temperature not exceeding 60° C.

* * * * *

UNITED STATES PATENT AND TRADEMARK OFFICE
CERTIFICATE OF CORRECTION

PATENT NO. : 4,992,588

DATED : Feb. 12, 1991

INVENTOR(S) : Josef MUELLER et al.

It is certified that error appears in the above-identified patent and that said Letters Patent is hereby corrected as shown below:

On the title page,
in the Abstract:

That part reading "O-acrylaminomethylbenzyl" should read -- o-acylaminomethylbenzyl --

Signed and Sealed this

Eighth Day of September, 1992

Attest:

DOUGLAS B. COMER

*Attesting Officer*    *Acting Commissioner of Patents and Trademarks*